(12) United States Patent
Presby

(10) Patent No.: US 8,999,153 B2
(45) Date of Patent: Apr. 7, 2015

(54) LIQUID WASTE TREATMENT SYSTEM

(71) Applicant: Presby Patent Trust, Whitefield, NH (US)

(72) Inventor: David W. Presby, Sugar Hill, NH (US)

(73) Assignee: Presby Patent Trust, Whitefield, NH (US)

( * ) Notice: Subject to any disclaimer, the term of this patent is extended or adjusted under 35 U.S.C. 154(b) by 272 days.

(21) Appl. No.: 13/650,792

(22) Filed: Oct. 12, 2012

(65) Prior Publication Data

US 2013/0092629 A1 Apr. 18, 2013

Related U.S. Application Data

(60) Provisional application No. 61/547,321, filed on Oct. 14, 2011.

(51) Int. Cl.
*C02F 3/00* (2006.01)
*C02F 3/30* (2006.01)

(52) U.S. Cl.
CPC .............. *C02F 3/30* (2013.01); *C02F 2203/006* (2013.01)

(58) Field of Classification Search
USPC .................. 405/47, 129.8; 210/605, 620, 150, 210/747.1, 433.1
See application file for complete search history.

(56) References Cited

U.S. PATENT DOCUMENTS

| | | |
|---|---|---|
| 3,160,425 A | 12/1964 | Sinnott |
| 3,440,822 A | 4/1969 | Hegler |
| 3,485,706 A | 12/1969 | Evans |
| 3,559,692 A | 2/1971 | Mantelet |
| 3,583,424 A | 6/1971 | Bryant |
| 3,830,373 A | 8/1974 | Sixt |
| 3,946,762 A | 3/1976 | Green |
| 3,961,153 A | 6/1976 | Smith et al. |
| 3,976,578 A | 8/1976 | Beane |
| 4,015,636 A | 4/1977 | Van Fossen |
| 4,019,326 A | 4/1977 | Herveling et al. |
| 4,140,422 A | 2/1979 | Crumpler et al. |
| 4,163,619 A | 8/1979 | Fales |
| 4,182,581 A | 1/1980 | Uehara et al. |

(Continued)

FOREIGN PATENT DOCUMENTS

| | | |
|---|---|---|
| CA | 1235911 | 5/1988 |
| JP | 2007-237118 | 9/2007 |

(Continued)

OTHER PUBLICATIONS

International Search Report and Written Opinion received in International Application No. PCT/US2011/036791, Date of mailing: Jan. 2, 2012, 10 pages.

(Continued)

*Primary Examiner* — Chester Barry
(74) *Attorney, Agent, or Firm* — Finch & Maloney PLLC

(57) ABSTRACT

A liquid waste treatment system is described. The system may include a first treatment conduit, a second treatment conduit, and at least one junction pipe disposed there between. In some instances, the system may include an upper junction pipe and a lower junction pipe disposed between a first and a second treatment conduit. In one or more embodiments, the system may be arranged in a substantially linear arrangement, such as a straight trench arrangement or a serial distribution arrangement. The system may reduce the need for additional treatment conduits.

17 Claims, 8 Drawing Sheets

(56) References Cited

U.S. PATENT DOCUMENTS

| | | |
|---|---|---|
| 4,204,967 A | 5/1980 | Bannister |
| 4,288,321 A | 9/1981 | Beane |
| 4,303,104 A | 12/1981 | Hegler et al. |
| 4,303,350 A | 12/1981 | Dix |
| 4,413,657 A | 11/1983 | Sasaki et al. |
| 4,523,613 A | 6/1985 | Fouss et al. |
| 4,529,414 A | 7/1985 | Naess |
| 4,662,778 A | 5/1987 | Dempsey |
| 4,904,113 A | 2/1990 | Goddard et al. |
| 4,909,665 A | 3/1990 | Caouette |
| 4,930,936 A | 6/1990 | Hegler et al. |
| 4,950,103 A | 8/1990 | Justice |
| 5,002,427 A | 3/1991 | Kambe et al. |
| 5,224,832 A | 7/1993 | Gonczy et al. |
| 5,263,792 A | 11/1993 | Davis et al. |
| 5,316,047 A | 5/1994 | Kanao |
| 5,429,752 A | 7/1995 | Presby |
| 5,480,260 A | 1/1996 | Shattuck et al. |
| 5,606,786 A | 3/1997 | Presby |
| 5,716,163 A | 2/1998 | Nichols et al. |
| 5,820,296 A | 10/1998 | Goughnour |
| 5,954,451 A | 9/1999 | Presby |
| 6,106,716 A | 8/2000 | Berkman |
| 6,190,548 B1 | 2/2001 | Frick |
| 6,290,429 B1 * | 9/2001 | Presby .................... 405/45 |
| 6,293,998 B1 | 9/2001 | Dolan et al. |
| 6,312,611 B1 * | 11/2001 | Bergman et al. ............ 210/793 |
| 6,315,493 B2 | 11/2001 | Malone et al. |
| 6,461,078 B1 | 10/2002 | Presby |
| 6,517,283 B2 | 2/2003 | Coffey |
| 6,613,954 B1 | 9/2003 | Horney et al. |
| 6,695,538 B1 | 2/2004 | Coffey |
| 6,749,745 B2 | 6/2004 | Jowett |
| 6,792,977 B2 | 9/2004 | Presby |
| 6,863,805 B1 | 3/2005 | Barreras et al. |
| 7,144,509 B2 | 12/2006 | Boyd et al. |
| 7,288,190 B2 | 10/2007 | Presby |
| 7,465,390 B2 | 12/2008 | Potts |
| 7,618,213 B2 | 11/2009 | Durkheim |
| 7,713,414 B2 * | 5/2010 | Presby .................... 210/605 |
| 7,744,756 B2 * | 6/2010 | Davis, Jr. ................ 210/170.08 |
| 7,967,979 B2 | 6/2011 | Grewal et al. |
| 8,342,212 B2 | 1/2013 | Presby |
| 2003/0113489 A1 | 6/2003 | Smith |
| 2003/0173293 A1 | 9/2003 | Potts |
| 2008/0202999 A1 | 8/2008 | Potts |

FOREIGN PATENT DOCUMENTS

| | | |
|---|---|---|
| WO | WO 2006-132790 | 12/2006 |
| WO | WO 2011-146470 | 11/2011 |

OTHER PUBLICATIONS

International Search Report and Written Opinion received in International Application No. PCT/US2006/019718, Date of mailing: Oct. 31, 2006, 5 pages.

International Search Report with Written Opinion, dated Apr. 8, 2013, received in PCT/US2012/059963, 16 pgs.

* cited by examiner

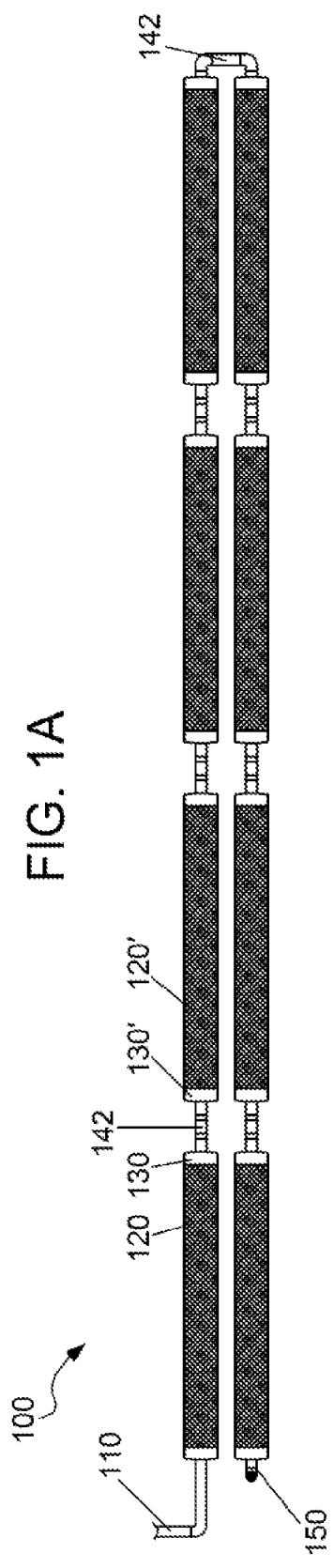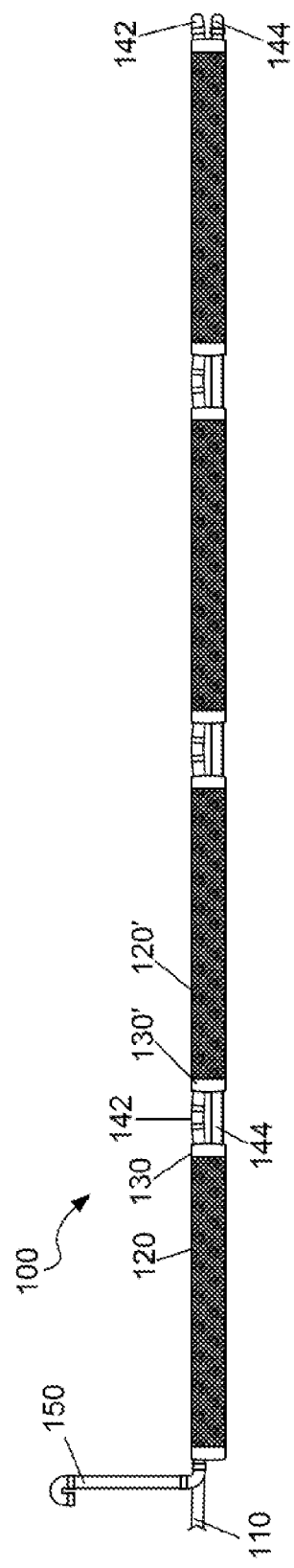

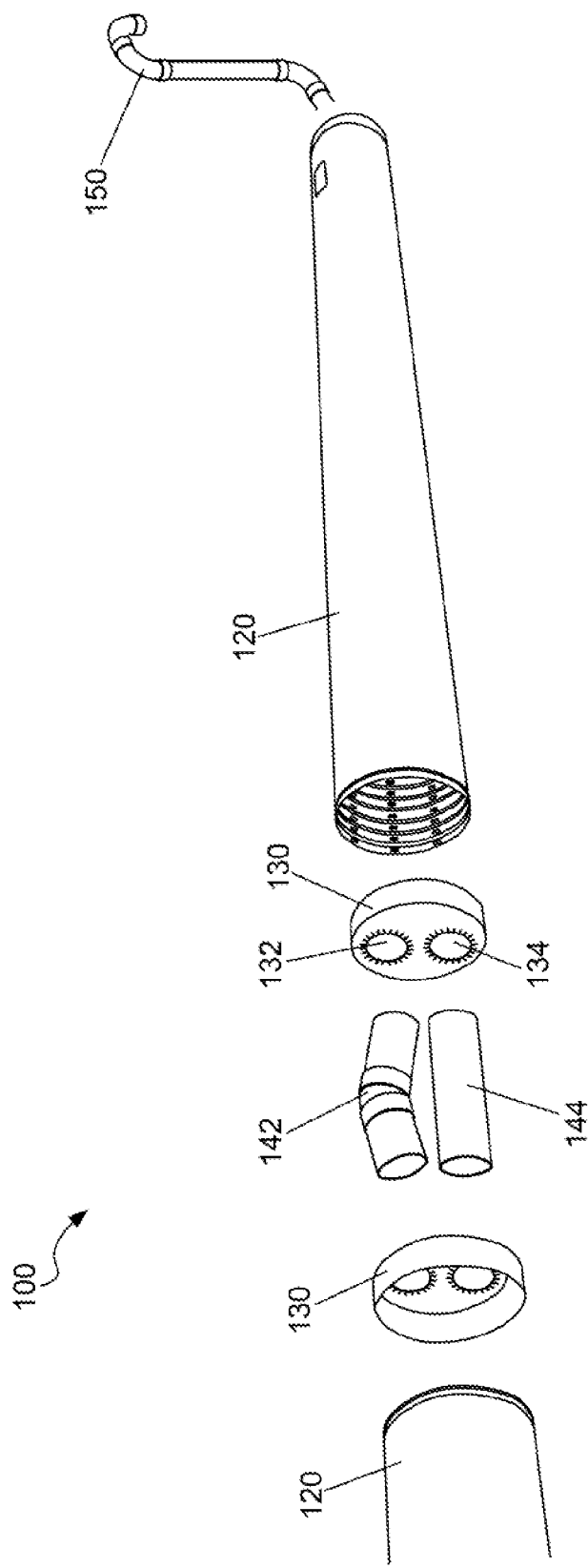

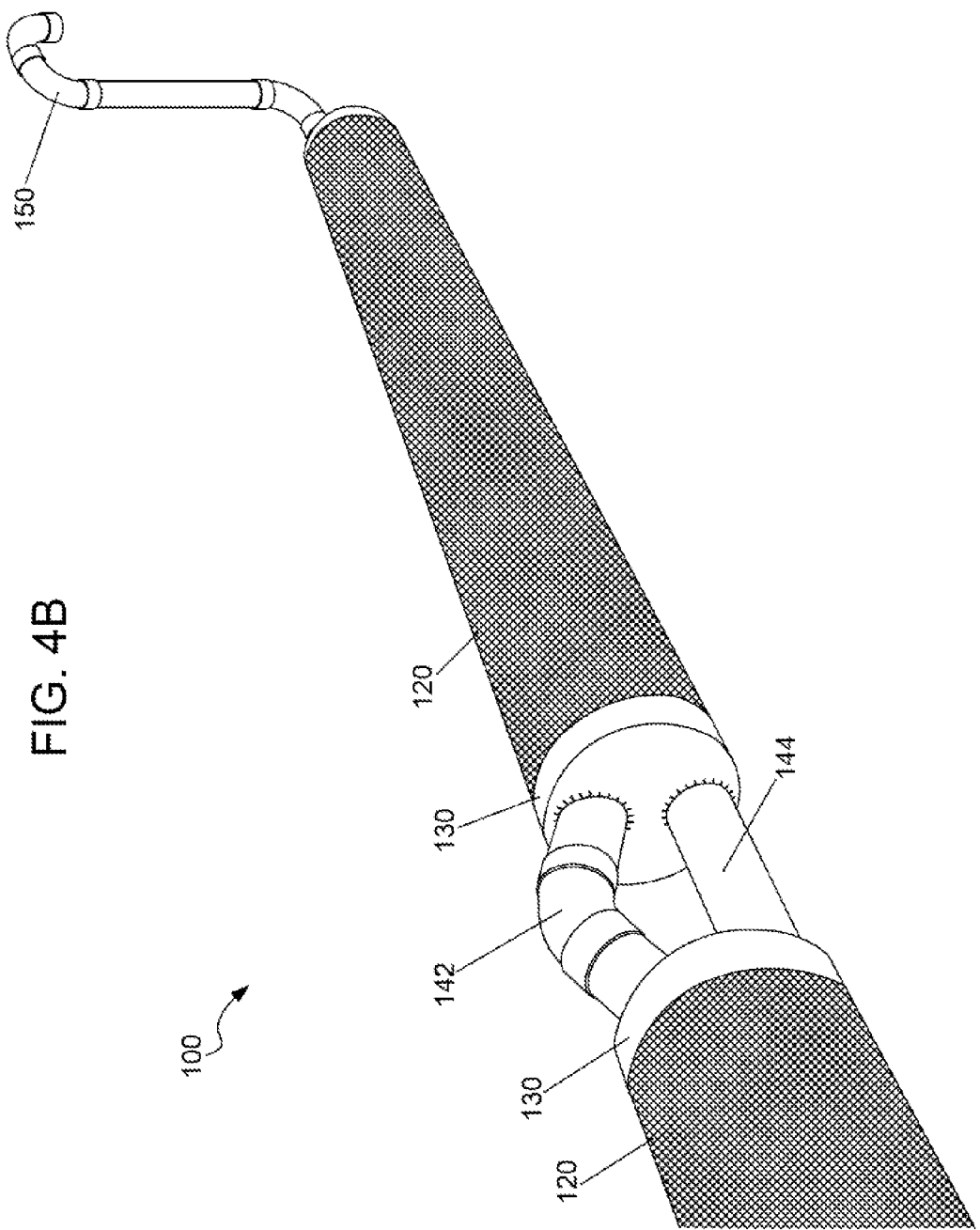

LIQUID WASTE TREATMENT SYSTEM

CROSS-REFERENCE TO RELATED APPLICATIONS

This application claims benefit of U.S. Provisional Patent Application Ser. No. 61/547,321, filed on Oct. 14, 2011. Each patent and patent application cited herein is hereby incorporated by reference in its entirety.

BACKGROUND

1. Field of the Invention

The invention relates to treatment of liquid waste and, in particular, to treatment of wastewater and septic effluent.

2. Discussion of Related Art

Common liquid waste treatment options include aerobic digestion and anaerobic digestion. In the bacterial process known as aerobic digestion, microorganisms break down biodegradable material in the presence of oxygen. In such aerobic processes, gaseous byproducts may be produced including, for example, carbon dioxide. In the bacterial process known as anaerobic digestion, microorganisms break down biodegradable material in the absence of oxygen. In such anaerobic processes, gaseous byproducts may be produced including, for example, methane.

SUMMARY

The subject matter of this application may involve, in some cases, interrelated products, alternative solutions to a particular problem, and/or a plurality of different uses of a single system or article.

In some embodiments, a system for treating liquid waste may include: a first treatment conduit in flow communication with a source of liquid waste, such first conduit having a first length and being constructed and arranged to perform aerobic and/or anaerobic treatment of such liquid waste; a second treatment conduit in flow communication with the first conduit, such second conduit constructed and arranged to perform aerobic and/or anaerobic treatment of such liquid waste; and at least one junction pipe operatively coupled between the first conduit and the second conduit, said at least one junction pipe having a length of at least 10% of the length of the first treatment conduit.

In some embodiments, the system may further include: a first end cap disposed on an end of the first conduit, said end cap comprising: a body constructed and arranged to be secured to the first conduit; an upper opening disposed in said body; and a lower opening disposed in said body and positioned beneath said upper opening; and a second end cap disposed on an end of the second conduit, said end cap comprising: a body constructed and arranged to be secured to the second conduit; an upper opening disposed in said body; and a lower opening disposed in said body and positioned beneath said upper opening.

In some embodiments, the system may further include: an upper junction pipe disposed in the upper opening of the first end cap and in the upper opening of the second end cap, said upper junction pipe permitting flow communication between the first conduit and the second conduit; and a lower junction pipe disposed in the lower opening of the first end cap and in the lower opening of the second end cap, said lower junction pipe permitting flow communication between the first conduit and the second conduit.

In one or more embodiments, the system may be constructed and arranged such that an opening of an end cap is configured to receive a junction pipe having a diameter of about four inches. In some instances, the system may be utilized to treat liquid waste comprising wastewater. In some specific example instances, a junction pipe may have a length that is at least 20% of the length of the first treatment conduit. In some specific example instances, the first treatment conduit is positioned at least 2 feet from the second treatment conduit. In some embodiments, the first treatment conduit is positioned at least 5 feet from the second treatment conduit.

In one or more embodiments, the system may be constructed and arranged such that a junction pipe is articulated. In some such embodiments, a junction pipe passes through the end cap at an angle that is not perpendicular to the end cap. In some embodiments, the articulated junction pipe has an apex at a point between the first and second treatment conduits. In some specific example instances, the lower junction pipe includes first and second ends and the first end extends through the first end cap by greater than 2 inches. In one or more embodiments, the lower junction pipe and the upper junction pipe each include first and second ends, and the first end of each junction pipe extends through the first end cap by greater than 2 inches. In some instances, the system may be constructed and arranged such that a junction pipe is comprised of a polymer. In some instances, the system may be constructed and arranged such that a junction pipe is comprised of cast iron. In some embodiments, the system may be constructed and arranged such that a junction pipe is flexible. In one or more embodiments, the system may be constructed and arranged such that the junction pipes are not fixed in place in relation to the end cap. In some instances, the system may be constructed and arranged such that a junction pipe forms a U-shape connecting two treatment conduits which are substantially parallel to each other. In some embodiments, the system may be constructed and arranged such that a junction pipe is curved. In one or more embodiments, the system may be constructed and arranged such that the treatment conduits are at essentially the same level. In some instances, the system may be positioned in the ground. In some embodiments, the system may be constructed and arranged such that the first conduit and/or second conduit have at least one layer, said layer being a permeable and/or semi-permeable material to promote aerobic and/or anaerobic treatment of the liquid waste.

In some embodiments, a system for treating liquid waste may include: a first conduit positioned in the ground, wherein said first conduit is in flow communication with a source of liquid waste; a second conduit positioned in the ground; a first junction pipe operatively coupled between the first and second conduit, said first junction pipe permitting flow communication of liquid waste and/or a gaseous volume between the first and second conduits; a second junction pipe operatively coupled between the first and second conduit, said second junction pipe permitting flow communication of liquid waste and/or a gaseous volume between the first and second conduits; and wherein the first and/or second conduit are constructed and arranged to perform aerobic and/or anaerobic treatment of said liquid waste. In one or more embodiments, the system may be constructed and arranged such that the first junction pipe is located above the second junction pipe.

In some embodiments the system may be constructed and arranged to include: a first end cap disposed on an end of the first conduit, said first end cap comprising: a body constructed and arranged to be secured to the first conduit; a first opening disposed in said body for receiving the first junction pipe; and a second opening disposed in said body for receiving the second junction pipe; and a second end cap disposed on an end of the second conduit, said second end cap comprising: a body constructed and arranged to be secured to the second conduit; a first opening disposed in said body for receiving the first junction pipe; and a second opening disposed in said body for receiving the second junction pipe.

In some embodiments, a method of making a liquid waste treatment system may include the steps of: positioning a first treatment conduit in the ground, wherein the first conduit is in flow communication with a source of liquid waste and arranged to perform aerobic and/or anaerobic treatment of such liquid waste; positioning a second treatment conduit in the ground, wherein the second conduit is arranged to perform aerobic and/or anaerobic treatment of such liquid waste; and operatively coupling the first conduit and the second conduit using at least one junction pipe, wherein the at least one junction pipe permits flow communication of liquid waste and/or a gaseous volume between the first and second conduit. In some embodiments, the method may further include the steps of: securing a first end cap on an end of the first conduit, said first end cap comprising: a body constructed and arranged to be secured to the first conduit; a first opening disposed in said body; and a second opening disposed in said body; and securing a second end cap on an end of the second conduit, said second end cap comprising: a body constructed and arranged to be secured to the second conduit; an first opening disposed in said body; and a second opening disposed in said body. In one or more embodiments, the method may further include the steps of: operatively coupling the first conduit and second conduit using a first junction pipe disposed in the first opening of the first end cap and in the first opening of the second end cap; and operatively coupling the first conduit and second conduit using a second junction pipe disposed in the second opening of the first end cap and in the second opening of the second end cap.

In some embodiments, a method for treating liquid waste may include the steps of: flowing a source of liquid waste into and/or through a first conduit; flowing the liquid waste into and/or through at least one junction pipe that is operatively coupled to the first conduit; flowing the liquid waste into and/or through a second conduit that is operatively coupled to the at least one junction pipe; and aerobically and/or anaerobically treating said liquid waste. In one or more embodiments, the method may further include the steps of: flowing the liquid waste and/or a gaseous volume through a lower junction pipe that is operatively coupled to the first conduit and second conduit; and flowing a gaseous volume and/or the liquid waste through an upper junction pipe that is operatively coupled to the first conduit and second conduit. In some embodiments, the method may further include the step of ventilating the first conduit and/or second conduit using a vent that is operatively coupled to said first and/or second conduit to permit air flow from the surrounding environs. In some instances, the upper junction pipe may be curved to assist with maintaining gas flow between the first and second conduits.

BRIEF DESCRIPTION OF THE DRAWINGS

FIG. 1A illustrates a top plan view of a liquid waste treatment system, configured in accordance with an embodiment of the present invention.

FIG. 1B illustrates a side plan view of the liquid waste treatment system illustrated in FIG. 1A.

FIG. 4A illustrates an exploded isometric perspective view of a liquid waste treatment system, configured in accordance with an embodiment of the present invention.

FIG. 4B illustrates an assembled isometric perspective view of the system of FIG. 4A.

Figure 2B:
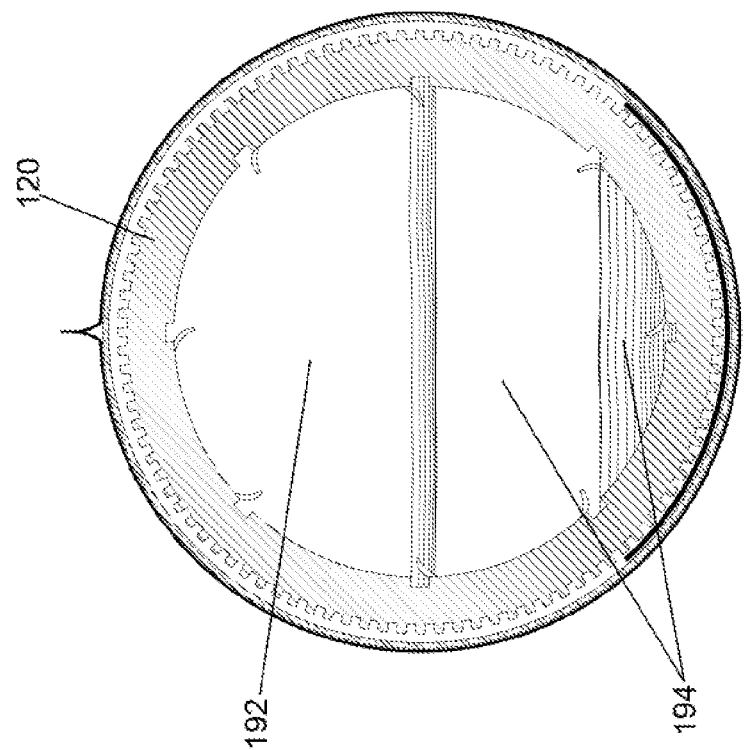
FIG. 2B illustrates a cross-section view depicting the conduit of FIG. 4A containing a volume of liquid waste and a gaseous volume.

These and other features of the present embodiments will be understood better by reading the following detailed description, taken together with the figures herein described. The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION

Techniques are disclosed for treating liquid waste. The techniques can be implemented, for example, to treat wastewater, septic effluent, and/or other liquid waste. The techniques may be utilized to promote aerobic and/or anaerobic digestion of biodegradable materials within the liquid waste. The techniques disclosed herein may be implemented in any number of system arrangements. Previously, sequential treatment conduits were joined directly together, providing for the maximum amount of treatment capacity in a given area. It has been found, however, that to cover a prescribed area, in some cases an adequate level of treatment can be obtained without maximizing the linear feet of treatment conduit in that space. This is in contrast to previous practices in which system designers were focused on maximizing the amount of treatment available over a given area.

In one or more embodiments, the techniques disclosed herein may be implemented to extend the overall length of a liquid waste treatment system without the need for inclusion of a large quantity of treatment conduits, thus reducing the overall cost of the system while increasing its size and/or range. In this manner, the system can cover a prescribed area without including more treatment conduits than is necessary to meet the desired level of performance. In such configurations, the treatment conduits may include less than 90%, less than 80%, less than 70%, or less than 60% of the length of the treatment system. Similarly, connectors may account for greater than 10%, greater than 20%, greater than 30%, greater than 40%, or greater than 50% of the length of the entire treatment system. The system may include pairs of junction pipes joining sequential treatment conduits together end-to-end. One of the junction pipes may be primarily for the transport of liquid while the other transports gases such as air or oxygen. The fluid flow in one of the paired pipes may be counter to the fluid flow in the other pipe. Although some aerobic treatment may occur in the junction pipes, the pipes serve to join treatment conduits together and the junction pipes need not add to the treatment capacity of the system. Numerous configurations and variations will be apparent in light of this disclosure.

FIG. 1A illustrates a top plan view of a liquid waste treatment system 100, configured in accordance with an embodiment of the present invention. FIG. 1B illustrates a side plan view of the liquid waste treatment system 100 illustrated in FIG. 1A. As can be seen, system 100 may include a liquid waste inlet 110, one or more treatment conduits 120 in flow communication with one another and with liquid waste inlet 110, and a vent 150. Examples of treatment conduits are described fully in co-owned U.S. patent application Ser. Nos. 11/915,150 and 13/109,695, which are hereby incorporated by reference in their entireties herein. In some embodiments, system 100 may be constructed and arranged to treat and/or process a liquid waste 194 (see FIG. 2B below), for example. System 100 may include additional, fewer, and/or different elements than those here described, and the foregoing is included merely for clarity of description and orientation by way of an illustrative example. The claimed invention is not intended to be limited to any particular liquid waste treatment system configurations, but can be used with numerous system arrangements in numerous applications.

The conduit(s) 120 used in the aerobic and/or anaerobic process may have any cross-sectional shape and size, and may be made of any solid material. For example, the conduit may be circular in cross-section and may have a diameter between about 15 cm and 45 cm. In one set of embodiments, the diameter is about 30 cm. The conduit may be provided in specific lengths that may be joined by connectors. For example, a conduit may be about 10 feet (3 meters) long. In addition, the conduit may be made of plastic, such as polypropylene or polyethylene. Perforations in the conduit may have any shape, such as circular and/or rectangular, and the perforations may have any functional size, for instance, of between about 1 mm and 20 mm. For example, the perforations may be round and have a diameter of about 10 mm. The conduit may also be corrugated. For example, the inner diameter and/or outer diameter of the conduit may vary sinusoidally along the axial length of the conduit. A suitable perforated conduit is ENVIROSEPTIC® pipe available from Presby Environmental, Inc., Whitefield, N.H.

In another aspect, one or more embodiments of a liquid waste treatment system 100 include an aerobic system and/or an anaerobic system. Both the aerobic and the anaerobic process or system may utilize different types of layers. Layers may include fabrics, aggregates and solids. Fabrics may be, for example, woven, non-woven, extruded, natural, synthetic or mixtures thereof. Aggregates can include, for example, sand, gravel, soil, glass beads, polymeric beads and other non-reactive particles. Solids may include, for example, monoliths such as carbon blocks, cardboard, polymeric blocks and inorganic blocks. One or more layers may be permeable, semi-permeable or impermeable to water. As used herein, a "permeable" material allows water to pass freely through the material with minimal or no retention. Permeable materials may be porous and may be of organic or inorganic materials. Examples of permeable materials include sand, fiberglass, glass beads, some woven and non-woven fabrics, such as layers of randomly distributed polymeric fibers and polymer mesh. Organic materials such as cotton, wool or hair may also be used to form a permeable layer. Permeable materials may include pores that allow for the free flow of water and/or other liquids while preventing the passage of some solids. Permeable layers may serve as supports for devices while allowing the passage of water there through. Permeable layers may also support microbial growth.

A "semi-permeable" material allows water to pass through the material after a period of retention. Water may pass through a semi-permeable material but most solids are retained. The period of liquid retention can allow for substantial wetting and microbial growth on the semi-permeable material. Such retention may also be useful for raising effluent to levels where it can be transferred to a subsequent conduit. The semi-permeable material may be hydrophilic or hydrophobic. An "impermeable" material prevents the flow of water (and other liquids) through the fabric and is designed to retain water indefinitely. In further aspects, a treatment system may include a ventilation component. One or more layers in the aerobic system and/or the anaerobic system may be a porous spacer layer. The spacer layer may be used to promote the flow of water and to provide space between adjacent bioactive layers.

Figure 2A:
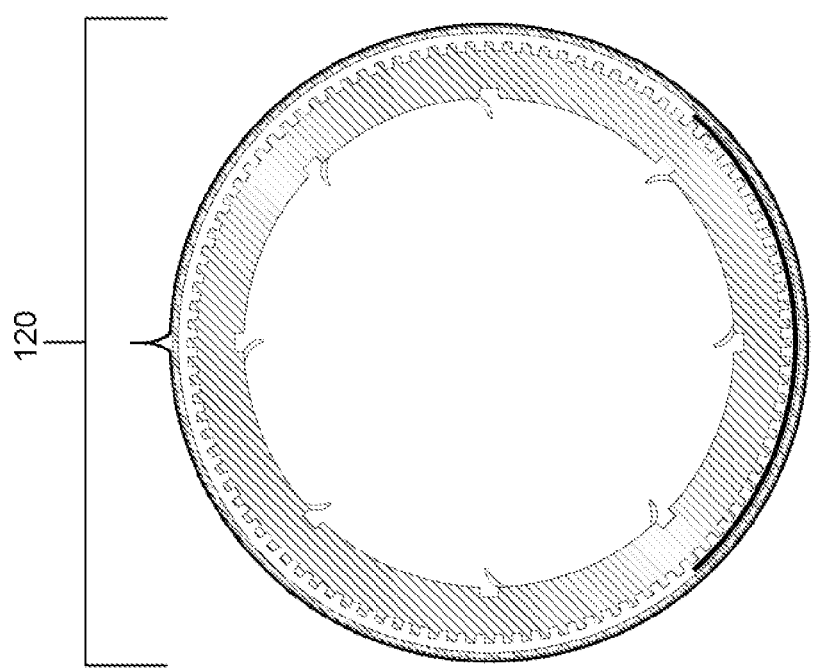
FIG. 2A illustrates a cross-section view of a treatment conduit, configured in accordance with an embodiment of the present invention.

FIG. 2A illustrates a cross-section view of a treatment conduit 120, configured in accordance with an embodiment of the present invention. FIG. 2B illustrates a cross-section view of the conduit 120 of FIG. 4A containing a volume of liquid waste 194 and a gaseous volume 192. In some embodiments, one or more conduits 120 within system 100 may be of the type disclosed in U.S. Pat. No. 6,461,078, titled "PLASTIC SEWAGE PIPE," the contents of which are hereby incorporated by reference in their entireties herein. In some embodiments, one or more conduits 120 of system 100 may be constructed and arranged to permit aerobic and/or anaerobic processes therein. In some instances, one or more conduits 120 may be configured to treat a volume of liquid waste 194.

Referring back to FIG. 1A, system 100 may include any number of treatment conduits 120 including, but not limited to, one conduit, two conduits, three conduits, four conduits, or five or more conduits. One or more of such conduits 120 may be in flow communication and/or be operatively coupled with another one or more of such conduits 120. In some embodiments, one or more of conduits 120 may be of substantially equal length, diameter, and/or other dimension as another one or more of such conduits 120. In some example instances, all conduits 120 of system 100 are of substantially the same dimensions and/or proportions.

In some embodiments, one or more portions of system 100 may be arranged, in part or in whole, in a substantially linear fashion. In other embodiments, one or more portions of system 100 may be arranged, in part or in whole, in a substantially non-linear fashion. In some instances, system 100 may include at least one portion arranged in a substantially linear fashion and at least one portion arranged in a substantially non-linear fashion. In some embodiments, one or more portions of system 100 may be disposed in the ground and/or above the ground. System 100 may be configured to function in numerous arrangements, including, but not limited to, a straight trench arrangement, a curved trench arrangement, a substantially horizontal planar arrangement on a hill, a bed arrangement, and/or a serial distribution arrangement.

As can be seen, in one or more embodiments, system 100 may be constructed and arranged to be substantially horizontal. In some embodiments, system 100 may be constructed and arranged to be parallel with the ground. In some instances, system 100 may be constructed and arranged to lie within ±1 degree, ±2 degrees, ±3 degrees, ±4 degrees, or ±5 degrees or more of horizontal. In some instances, system 100 may be constructed and arranged to minimize, counteract, and/or prevent any substantial angle of inclination and/or declination. In any given embodiment, such substantially horizontal arrangement may assist, for example, with even distribution and/or flow of liquid waste 194 within system 100 so that waste treatment can occur throughout the system 100.

Liquid waste inlet 110 may be constructed and arranged to be in flow communication with a source (not shown) of liquid waste 194. Liquid waste inlet 110 may be disposed between the liquid waste source and one or more treatment conduits 120. Liquid waste inlet 110 may be configured to permit liquid waste 194 to enter and/or flow into one or more conduits 120. In some embodiments, liquid waste inlet 110 may be operatively coupled to a serial distribution box 160, as discussed in greater detail below with reference to FIGS. 6A and 6B.

In some embodiments, at least one treatment conduit 120 may be spaced and/or arranged equidistantly from another treatment conduit 120', as shown. In some instances, all conduits 120 of system 100 may be spaced and/or arranged equidistantly from one another. In any given embodiment, such equidistant spacing and/or arrangement may assist, for example, with even distribution and/or flow of liquid waste 194 within system 100.

In embodiments of system 100 including a vent 150, such vent 150 may be operatively coupled with one or more conduits 120. In some instances, vent 150 may be operatively coupled with one or more conduits 120 that are distal and/or furthest away in terms of flow communication from liquid waste inlet 110. Such vent 150 may be constructed and arranged to function as an inlet permitting flow of air from the surrounding environs into a portion and/or the entirety of system 100. Drawing of air into system 100 via vent 150, when included, may assist, for example, with aerobic processes within conduits 120.

Figure 3:
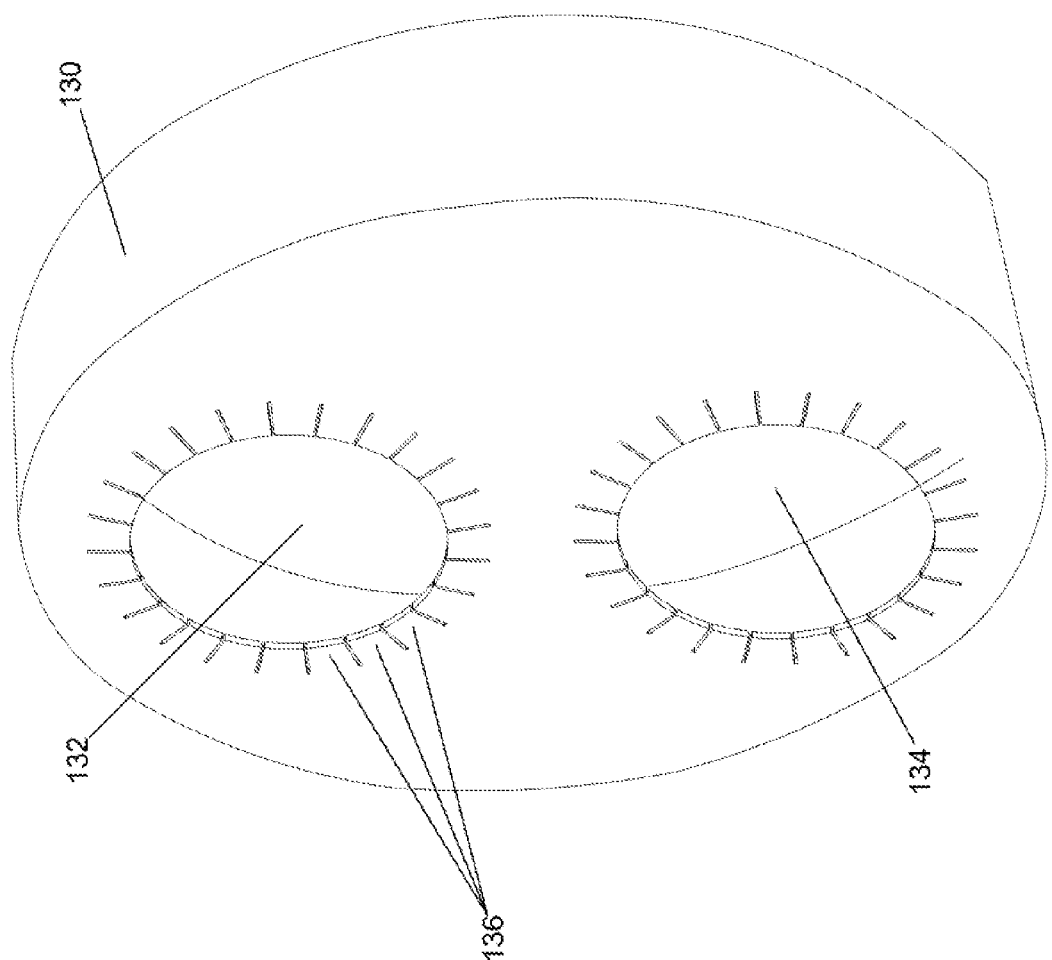
FIG. 3 illustrates an isometric perspective view of an end cap, configured in accordance with an embodiment of the present invention.

Referring back to FIGS. 1A and 1B, for example, system 100 may include one or more end caps 130. FIG. 3 illustrates an isometric perspective view of an end cap 130, configured in accordance with an embodiment of the present invention. In some embodiments, one or more end caps 130 may be of the type disclosed in U.S. Pat. No. 6,792,977, titled "END CAP FOR A CORRUGATED CONDUIT," the contents of which are hereby incorporated by reference in their entireties herein.

In some embodiments, end cap 130 may be constructed and arranged as a body including one or more openings 132 and/or 134. In some embodiments, openings 132 and/or 134 may be defined, in part or in whole, by prefabricated holes cut out from the body of end cap 130, removable inserts stamped out of the body of end cap 130, and/or perforated outlines disposed in the body of end cap 130. In some instances in which end cap 130 includes both an opening 132 and an opening 134, opening 132 may be positioned substantially above opening 134. For example, the circumference of opening 132 may be greater than 1 inch, greater than 2 inches, greater than 3 inches, or greater than 4 inches from the circumference of opening 134. Openings 132 and 134 may be spaced substantially distal from one another, while in other embodiments, openings 132 and 134 may be spaced substantially proximate one another. In one or more embodiments, openings 132 and/or 134 may be constructed and arranged to receive a pipe, such as junction pipes 142 and/or 144, for example, discussed in greater detail below with reference to FIGS. 4A and 4B.

Openings 132 and/or 134 may be of any shape desired. In some embodiments, openings 132 and/or 134 may be configured in substantially the same shape as junction pipes 142 and/or 144 to facilitate operative coupling there between. In embodiments in which junction pipes 142 and/or 144 are of substantially circular cross-section, openings 132 and/or 134 may be similarly configured. In embodiments in which junction pipes 142 and/or 144 are of non-circular cross-section, openings 132 and/or 134 may be similarly configured so that pipes 142 and 144 can fit snugly into the openings.

In some embodiments, end cap 130 may include a plurality of flexible fingers 136 disposed about the perimeter of openings 132 and/or 134. In some such embodiments, openings 132 and/or 134 including flexible fingers 136 may be constructed and arrange to receive a pipe, such as junction pipes 142 and/or 144, for example. Upon insertion and/or retraction of a pipe (such as junction pipes 142 and/or 144), flexible fingers 136 may be bent in either direction about their point of connection to the body of end cap 130.

In some embodiments, openings 132 and/or 134 may be constructed and arranged to form, for example, a friction fit, a snap fit, a retainer-and-tab fit, a screw fit, or any other suitable fit sufficient to maintain operative coupling between junction pipes 142 and/or 144 and end cap 130. In some instances, openings 132 and/or 134 may be constructed and arranged to form a liquid-tight seal with the exterior of junction pipes 142 and/or 144, thereby preventing any liquid waste 194 flowing between conduits 120 from leaking out from the interface of junction pipes 142 and/or 144 and end cap 130. In some such embodiments, one or more openings 132 and/or 134 may include an O-ring or other suitable gasket material disposed therein and configured to engage the exterior of junction pipes 142 and/or 144, when inserted, to minimize and/or prevent such leakage. In other embodiments, the junction between the junction pipes 142 and/or 144 and openings 132 and/or 134 is secure but not necessarily liquid-tight. It has been found that after installation in the ground an effective seal (e.g., soil, sand, a biomaterial layer, etc.) is formed around the opening 132 and/or 134 that prevents excessive leakage of liquid waste 194 from the system 100. In some instances, junction pipes 142 and/or 144 may be removed readily from end caps 130 without damaging the junction pipes 142 and/or 144 and/or end caps 130.

End cap 130 may be constructed of a material that is non-reactive with any or all of the one or more materials from which system 100 may be constructed. In some instances, end cap 130 may be constructed of the same one or more materials from which conduit 120 may be constructed. Such materials may include, for example, polymers, metals, alloys, and clay. Suitable polymers may include, for example, PVC, ABS, and polyolephins.

FIG. 4A illustrates an exploded isometric perspective view of a liquid waste treatment system 100, configured in accordance with an embodiment of the present invention. FIG. 4B illustrates an assembled isometric perspective view of the system 100 of FIG. 4A. As can be seen, end cap 130 may be configured to engage, fit on, and/or operatively couple with an end of a conduit 120. In some instances, end cap 130 may be configured in substantially the same shape as conduit 120 to facilitate such operative coupling. In embodiments in which conduit 120 may be substantially circular in cross-section, end cap 130 may be similarly configured. In embodiments in which conduit 120 may be non-circular in cross-section, end cap 130 may be similarly configured. In some embodiments, end cap 130 may be constructed and arranged to form, for example, a friction fit, a snap fit, a retainer-and-tab fit, a screw fit, or any other suitable fit sufficient to maintain operative coupling between end cap 130 and an end of conduit 120. In some instances, end cap 130 may be constructed and arranged to form a liquid-tight seal with an end of conduit 120, thereby preventing any liquid waste 194 contained within conduit 120 from leaking out from the interface of end cap 130 and conduit 120. In some such embodiments, one or more of conduit 120 and/or end cap 130 may include an O-ring or other suitable gasket material disposed thereat and configured so as to minimize and/or prevent leakage of liquid waste 194 from the interface of end cap 130 and conduit 120. In other embodiments, the junction between conduit 120 and end cap 130 is secure but not necessarily liquid-tight. It has been found that after installation in the ground an effective seal (e.g., soil, sand, a biomaterial layer, etc.) is formed around end cap 130 and/or conduit 120 that prevents excessive leakage of liquid waste 194 from the system 100. In some instances, end cap 130 may be removed readily from conduit 120 without damaging the end cap 130 and/or conduit 120.

System 100 may include one or more junction pipes 142 and/or 144. In some embodiments, junction pipes 142 and/or 144 may be substantially circular in cross-section. In some such embodiments, junction pipes 142 and/or 144 may have a substantially constant circumference. In some instances, junction pipes 142 and/or 144 may be of about 4 inches in diameter, though other configurations of greater and/or lesser diameters are possible and deemed within the scope of this invention. In other embodiments, junction pipes 142 and/or 144 may be non-circular in cross-section. Junction pipes 142 and/or 144 may be constructed and arranged to fit within openings 132 and/or 134 of end cap 130. When installed, the junction pipes 142 and 144 may be oriented vertically in relation to each other so that, when looking at end cap 130, the upper junction pipe 142 is at the 12 o'clock position and the lower junction pipe 144 is at the 6 o'clock position.

Junction pipes 142 and/or 144 may be constructed of a material that is non-reactive with any or all of the one or more materials from which system 100 may be constructed. In some instances, junction pipes 142 and/or 144 may be constructed of the same one or more materials from which end cap 130 may be constructed. In some embodiments, junction pipes 142 and/or 144 may be constructed of polymeric materials, including, but not limited to, polyvinyl chloride (PVC), or of metallic materials, including, but not limited to, copper or cast iron. In one or more embodiments, junction pipe 142 and/or 144 may be of rigid construction, flexible construction, or other suitable construction configured to maintain flow communication in system 100.

Junction pipes 142 and/or 144 may be of any desired configuration including, but not limited to, a straight configuration, a curved configuration, an angled configuration, and/or an articulated configuration. Junction pipes 142 and/or 144 may be straight, connecting two treatment conduits 120 aligned with each other or may include a right angle for connecting two treatment conduits 120 positioned at right angles to each other. Junction pipes 142 and/or 144 also may be U-shaped, including two right angles, to connect two treatment conduits 120 that are aligned side-by-side. Upper junction pipe 142 may be articulated so that, when installed, junction pipe 142 has an apex at a point between the two treatment conduits 120 being connected by junction pipe 142. While junction pipes 142 and/or 144 may pass through the end cap 130 at an angle substantially normal to the surface of the end cap 130, an articulated junction pipe 142 and/or 144 may pass through the end cap 130 at an angle that is not in alignment with the axis of the treatment conduit 120. Junction pipes 142 and/or 144 may be fixed to the end caps 130 using, for example, polymeric cement or a physical retainer such as tabs or fingers. Alternatively, junction pipes 142 and/or 144 are not fixed to the end caps 130 and are free to slide back and forth in relation to the end caps 130. One or more of junction pipes 142 and/or 144 may be constructed and arranged as a unitary piece or as an assembly of multiple constituent components. The unitary assembly may include one or two junction pipes 142 and/or 144 and one or two end caps 130. In some example embodiments, junction pipe 142 may be constructed and arranged to be operatively inserted into opening 132. In some example embodiments, junction pipe 144 may be constructed and arranged to be operatively inserted into opening 134. Junction pipes 142 and/or 144 may extend through the openings 132 and/or 134 by, for example, greater than 1 inch, greater than 2 inches, greater than 5 inches, or greater than 10 inches.

Figure 5A:
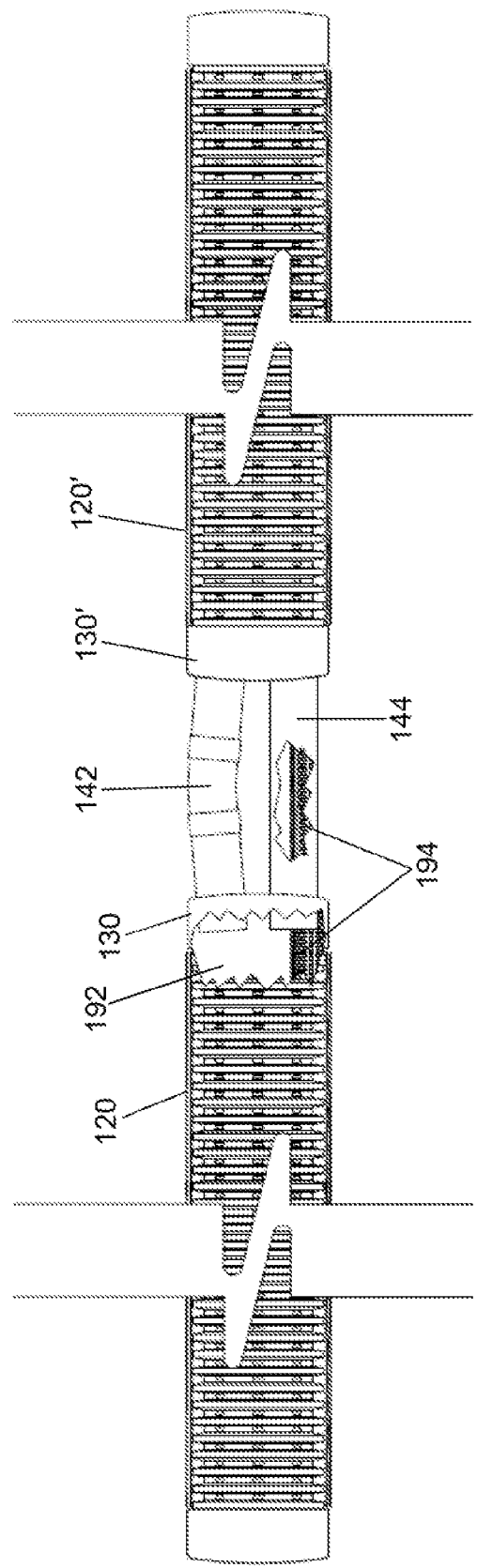
FIG. 5A illustrates a partial cutaway view of an assembled liquid waste treatment system, configured in accordance with an embodiment of the present invention.
Figure 5B:
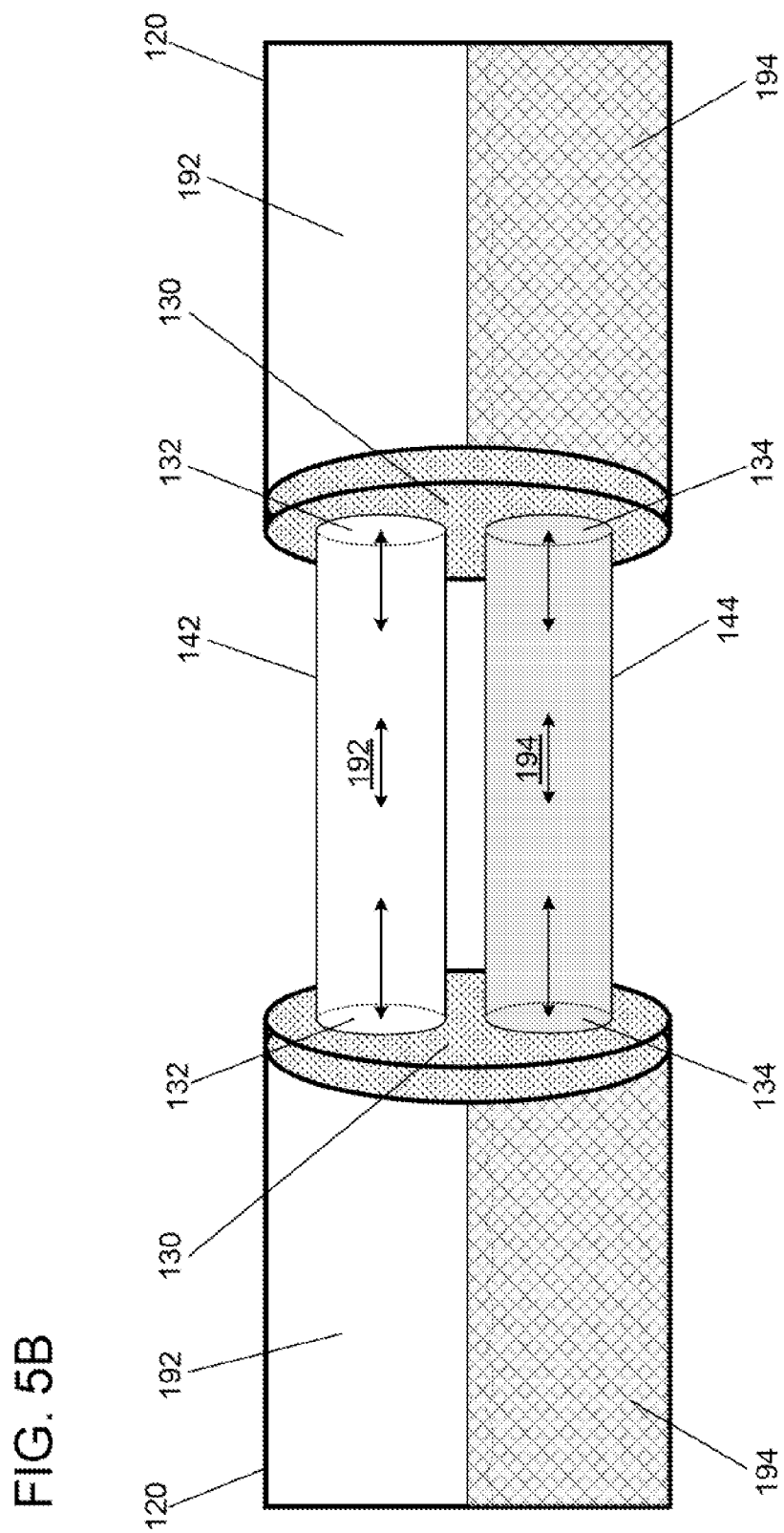
FIG. 5B illustrates a partial cutaway view of the system in FIG. 5A.

FIG. 5A illustrates a partial cutaway view of an assembled liquid waste treatment system 100, configured in accordance with an embodiment of the present invention. As illustrated, junction pipe 142 can be oriented directly above junction pipe 144 so that they are in vertical alignment when the system 100 is installed. FIG. 5B illustrates a partial cutaway view of the system 100 in FIG. 5A. As can be seen, junction pipe 142 may be configured to primarily permit flow communication of a gaseous volume 192 between conduits 120. Under some conditions, such as the presence of a sufficiently high level of liquid waste 194 in conduits 120, junction pipe 142 may secondarily permit flow communication of a liquid waste volume 194 between conduits 120. To avoid buildup and/or settling of liquid waste 194 within junction pipe 142, in some embodiments, junction pipe 142 may be angled, curved, or otherwise non-linear, thereby permitting clearing thereof via gravitational flow.

Junction pipe 144 may be configured to primarily permit flow communication of a liquid waste volume 194 between conduits 120. In some instances, such as the presence of a sufficiently low level of liquid waste 194 in conduits 120, junction pipe 144 may secondarily permit flow communication of a gaseous volume 192 between conduits 120.

Junction pipes 142 and/or 144 may be configured to be operatively inserted into openings 142 and/or 144 to any desired depth. In some instances, junction pipes 142 and/or 144 may be insertable to a depth of about 2-4 inches into end caps 130. The distance between end cap 130 and 130' can be adjusted by inserting junction pipes 142 and 144 to different depths. This can allow for a single length junction pipe in designs that might require different distances between two facing end caps 130. In some embodiments in which junction pipe 142 may be angled, curved, or otherwise non-linear, it may be desirable to insert junction pipe 142 only to a depth so that its ends do not dip below the level of liquid waste 194 in conduits 120. In some such instances, this configuration may assist with maintaining gas flow and an aerobic environment within conduits 120 of system 100.

Figure 6A:
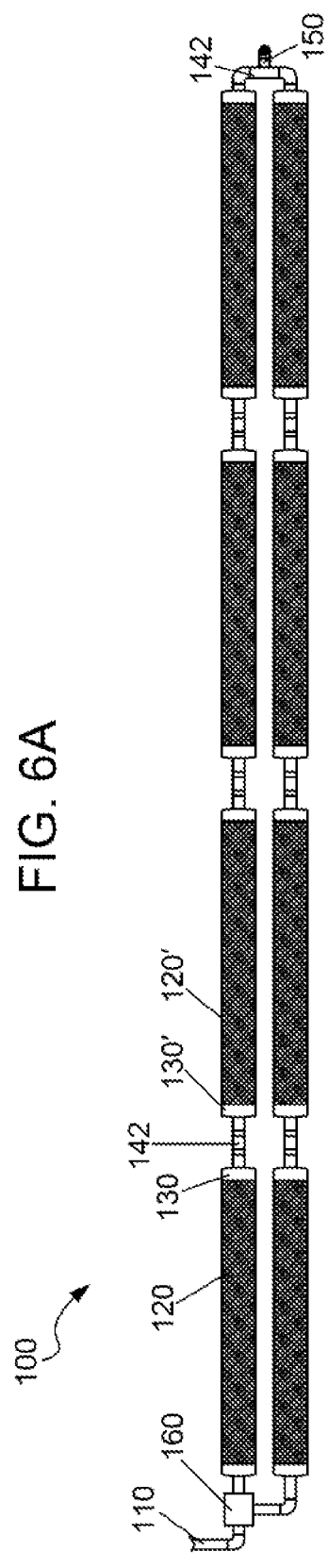
FIG. 6A illustrates a top plan view of a liquid waste treatment system, configured in accordance with an embodiment of the present invention.
Figure 6B:
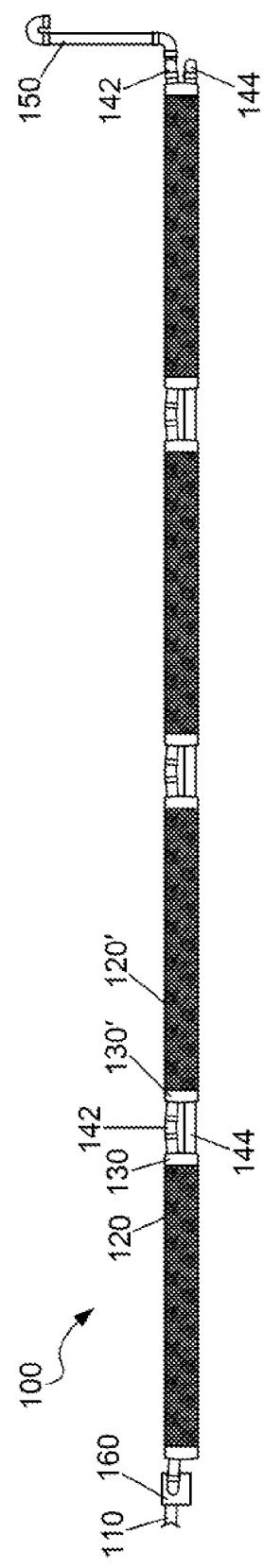
FIG. 6B illustrates a side plan view of the system illustrated in FIG. 6A.

FIG. 6A illustrates a top plan view of a liquid waste treatment system 100, configured in accordance with an embodiment of the present invention. FIG. 6B illustrates a side plan view of the system 100 illustrated in FIG. 6A. As can be seen, in some embodiments system 100 may be configured in a serial distribution arrangement and include a liquid waste inlet 110, a serial distribution box 160, one or more treatment conduits 120 in flow communication with one another and with serial distribution box 160, and a vent 150.

In embodiments including a serial distribution box 160, liquid waste inlet 110 may be constructed and arranged to be in flow communication therewith. In such embodiments, liquid waste inlet 110 may permit flow of liquid waste 194 from a source (not shown) to serial distribution box 160. In some embodiments, serial distribution box 160 may be constructed and arranged to be in flow communication with one or more treatment conduits 120. In such embodiments, liquid waste 194 may be permitted to flow from liquid waste inlet 110 through serial distribution box 160 into one or more treatment conduits 120.

In embodiments of system 100 including a serial distribution box 160 and a vent 150, such vent 150 may be operatively coupled with one or more conduits 120. In some instances, vent 150 may be operatively coupled with one or more conduits 120 that are distal and/or furthest away in terms of flow communication from serial distribution box 160. Such vent 150 may be constructed and arranged to function as an inlet permitting flow of air from the surrounding environs into a portion and/or the entirety of system 100. Drawing of air into system 100 via vent 150 may assist, for example, with aerobic processes within conduits 120.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

While several embodiments of the present invention have been described and illustrated herein, those of ordinary skill in the art readily will envision a variety of other means and/or structures for performing the functions and/or obtaining the results and/or one or more of the advantages described herein, and each of such variations and/or modifications is deemed to be within the scope of the present invention. More generally, those skilled in the art readily will appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. Therefore, it is to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents, patent applications, and publications that are cited or referred to in this application are incorporated in their entirety herein by reference.

What is claimed is:

1. A system for treating liquid waste, the system comprising:
   a first treatment conduit in flow communication with a source of liquid waste, the first treatment conduit having a first length and being configured to perform aerobic and/or anaerobic treatment of such liquid waste;
   a first end cap disposed on an end of the first treatment conduit, the first end cap comprising:
      a body configured to be secured to the first treatment conduit;
      an upper opening disposed in that body; and
      a lower opening disposed in that body and positioned beneath the upper opening;
   a second treatment conduit in flow communication with the first treatment conduit, the second treatment conduit configured to perform aerobic and/or anaerobic treatment of such liquid waste;
   a second end cap disposed on an end of the second treatment conduit, the second end cap comprising:
      a body configured to be secured to the second treatment conduit;
      an upper opening disposed in that body; and
      a lower opening disposed in that body and positioned beneath the upper opening;
   an upper junction pipe disposed in the upper opening of the first end cap and in the upper opening of the second end cap, the upper junction pipe configured to permit flow communication between the first treatment conduit and the second treatment conduit; and
   a lower junction pipe disposed in the lower opening of the first end cap and in the lower opening of the second end cap, the lower junction pipe configured to permit flow communication between the first treatment conduit and the second treatment conduit;
      wherein at least one of the upper and lower junction pipes has a length of at least 10% of the length of the first treatment conduit.

2. The system of claim 1, wherein the liquid waste comprises wastewater.

3. The system of claim 1, wherein the first treatment conduit is positioned at least 2 feet from the second treatment conduit.

4. The system of claim 1, wherein at least one of the upper and lower junction pipes is articulated.

5. The system of claim 1, wherein at least one of the upper and lower junction pipes passes through at least one of the first and second end caps at an angle that is not perpendicular to the at least one of the first and second end caps.

6. The system of claim 4, wherein at least one of the articulated upper and lower junction pipes has an apex at a point between the first and second treatment conduits.

7. The system of claim 1, wherein the lower junction pipe and the upper junction pipe each include first and second ends, and wherein the first end of at least one of the upper and lower junction pipes extends through at least one of the first and second end caps by greater than 2 inches.

8. The system of claim 1, wherein at least one of the upper and lower junction pipes is not fixed in place in relation to at least one of the first and second end caps.

9. The system of claim 1, wherein at least one of the first and second treatment conduits includes at least one layer, the at least one layer comprising at least one of a permeable material and a semi-permeable material configured to promote aerobic and/or anaerobic treatment of the liquid waste.

10. A system for treating liquid waste, the system comprising:
- a first conduit positioned in the ground, wherein said first conduit is in flow communication with a source of liquid waste;
- a second conduit positioned in the ground;
- a first junction pipe operatively coupled between the first and second conduit, said first junction pipe permitting flow communication of liquid waste and/or a gaseous volume between the first and second conduits; and
- a second junction pipe operatively coupled between the first and second conduit, said second junction pipe permitting flow communication of liquid waste and/or a gaseous volume between the first and second conduits;
- wherein the first and/or second conduit are constructed and arranged to perform aerobic and/or anaerobic treatment of said liquid waste.

11. The system of claim 10, wherein at least one junction pipe is curved.

12. The system of claim 10, wherein at least one of the junction pipes is flexible.

13. The system of claim 10, wherein at least one of the junction pipes forms a U-shape connecting two treatment conduits which are substantially parallel to each other.

14. The system of claim 10, wherein the first conduit and/or second conduit have at least one layer, said layer being a permeable and/or semi-permeable material to promote aerobic and/or anaerobic treatment of the liquid waste.

15. The system of claim 10, further comprising:
- a first end cap disposed on an end of the first conduit, said first end cap comprising:
  - a body constructed and arranged to be secured to the first conduit;
  - a first opening disposed in said body for receiving the first junction pipe; and
  - a second opening disposed in said body for receiving the second junction pipe; and
- a second end cap disposed on an end of the second conduit, said second end cap comprising:
  - a body constructed and arranged to be secured to the second conduit;
  - a first opening disposed in said body for receiving the first junction pipe; and
  - a second opening disposed in said body for receiving the second junction pipe.

16. The system of claim 1 further comprising a vent pipe in flow communication with at least one of the first and second treatment conduits.

17. The system of claim 1 further comprising a distribution box in flow communication with at least one of the first and second treatment conduits.

* * * * *